United States Patent [19]

McGuinness et al.

[11] Patent Number: 4,793,334

[45] Date of Patent: Dec. 27, 1988

[54] CERVICAL BRACE

[76] Inventors: Charles G. McGuinness, 6 High St., Hicksville, Long Island, N.Y. 11801; John J. McCourt, Silverstream, Monaghan, Ireland

[21] Appl. No.: 85,587

[22] Filed: Aug. 14, 1987

[30] Foreign Application Priority Data

Jul. 22, 1986 [IE] Ireland .................................. 1938/86

[51] Int. Cl.⁴ .............................................. A61F 5/04
[52] U.S. Cl. .................................................. 128/87 B
[58] Field of Search ................. 128/75, 87 B, DIG. 23

[56] References Cited

U.S. PATENT DOCUMENTS

| 197,243 | 11/1877 | Boylston | 128/DIG. 23 |
| 460,451 | 9/1891 | Shaw | 128/DIG. 23 |
| 1,397,499 | 11/1921 | Breanan | 128/DIG. 23 |
| 2,735,424 | 2/1956 | Benjamin | 128/87 B |
| 2,736,314 | 2/1956 | Hale | 128/87 B |
| 2,820,455 | 1/1958 | Hall | 128/DIG. 23 |
| 3,724,452 | 4/1973 | Nitschke | 128/75 |
| 4,383,523 | 5/1983 | Schurman | 128/87 B |

Primary Examiner—Robert A. Hafer
Assistant Examiner—Michael Brown
Attorney, Agent, or Firm—Collard, Roe & Galgano

[57] ABSTRACT

The invention provides a cervical brace comprising a harness which comprises a framework and straps for securing the framework to the body, and a chin support member supported on a strut which is releasably and pivotally mounted to the framework. A brace member extending from the strut provides for pivotal movement of the strut, thereby permitting the chin support member to be moved inwardly and outwardly relative to a wearer to snugly engage the wearers chin.

18 Claims, 4 Drawing Sheets

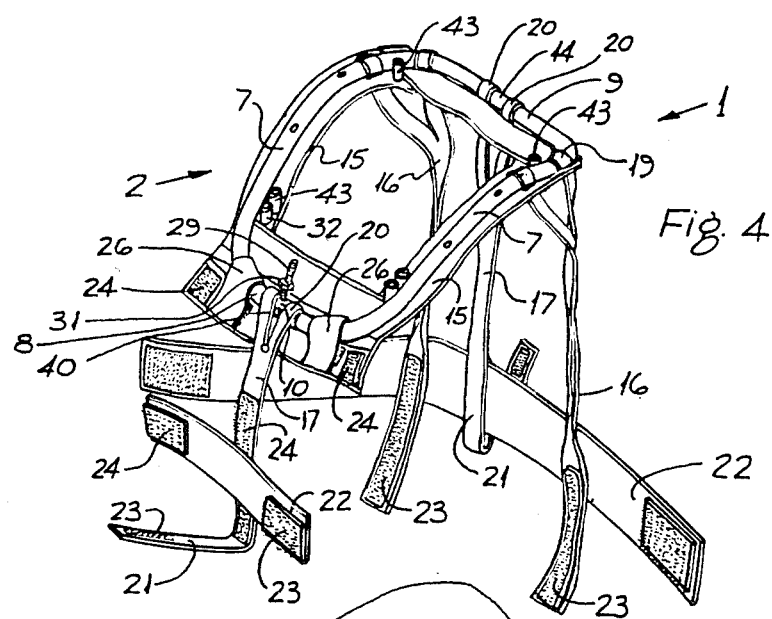
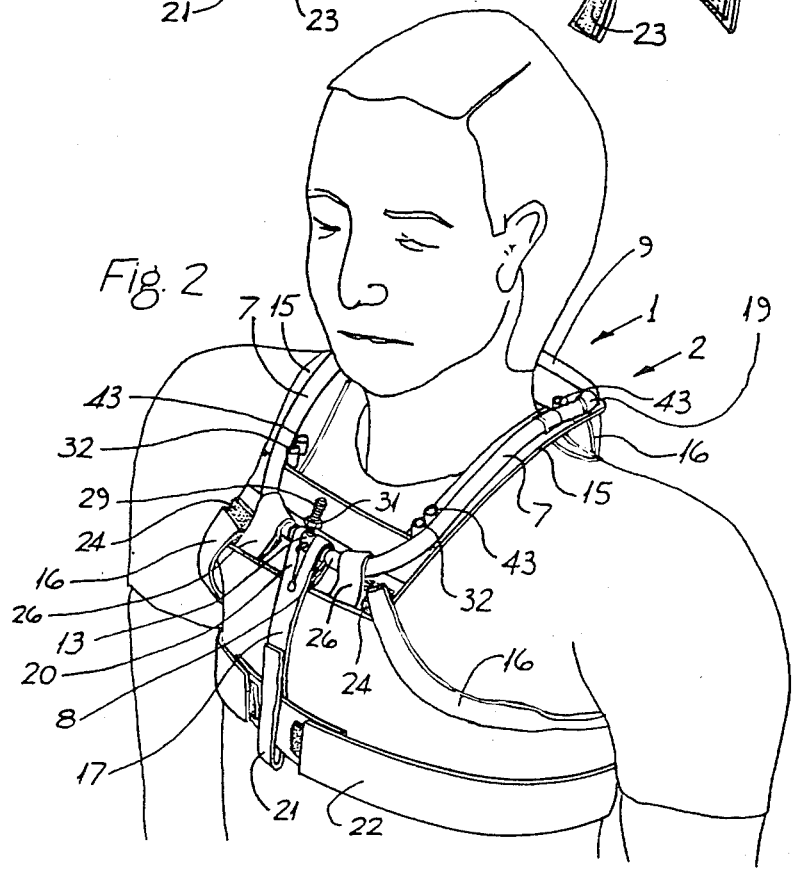

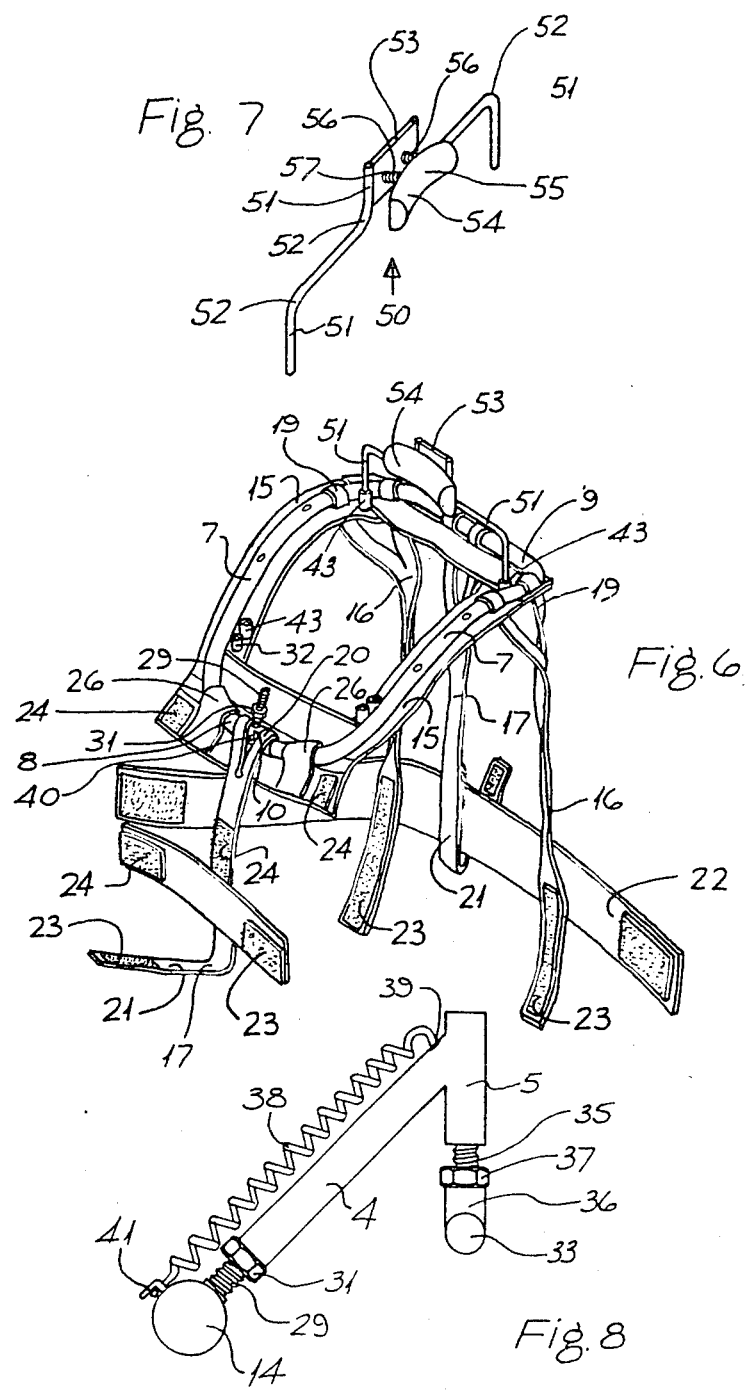

CERVICAL BRACE

FIELD OF THE INVENTION

The present invention relates to a cervical brace. In general, cervical braces are worn to correct or ease discomfort from spinal injuries, particularly spinal injuries in the area of the neck vertebrae. In particular, cervical braces are commonly used to rectify any spinal damage caused as a result of whiplash injury.

BACKGROUND TO THE INVENTION

There are a number of types of such braces. For example, one type comprises a relatively stiff collar worn round the neck, which extends between the shoulders and the jawbone and chin of the wearer. While such collars do give a certain amount of support, they do not provide for adjustment to accommodate varying lengths of different people's necks. Thus, on some they may be relatively comfortable, while on others they can cause considerable discomfort. For example, in the case of an individual with a relatively short neck, such a collar may cause the chin to be retained at a totally incorrect angle. Further, for an individual with a relatively long neck, the chin may also be supported at the wrong angle. A further problem with such collars is that they are clearly visible for all to see, and, in general, are relatively unsightly. Furthermore, because they are worn completely around the neck, there is very little circulation of air between the collar and the neck. Accordingly, they tend to induce perspiration in the neck area which further leads to discomfort. Various attempts have been made to overcome the problems of such collars. Examples of such attempts are given in the following U.S. Pat. specifications, namely, U.S. Pat. Nos. 3,724,452, 3,945,376, 4,383,523 and 4,628,913. In general, these cervical braces comprise a harness for mounting on the torso of the body, and a chin support member for supporting the chin of the wearer. The chin support member is mounted on a support bar which is adjustable upwardly and downwardly to accommodate wearers with different lengths of neck. However, while these devices partly overcome the problems of stiff collars in that at least the height at which the wearer's chin is supported can be adjusted, nonetheless, they do not provide for the different positions which individuals chins may take up, in other words, the position of a wearer's chin front to back. Accordingly, while the chin supports may be adjusted to accommodate different heights of chins, this does not ensure that the chin support will accurately or correctly engage the wearer's chin. For example, if a wearer has a chin which projects more than normally, or a wearer has a chin which projects less than normally, then the chin support will not adequately support the wearer's chin.

Furthermore, while these devices assist in supporting a patient's chin, they do not provide any other support besides a support for the wearer's occiput.

There is therefore a need for cervical brace which overcomes the problems of known cervical braces. The present invention is directed towards providing such a cervical brace.

OBJECTS OF THE INVENTION

One object of the invention is to provide a cervical brace which comprises a chin support member for supporting a wearer's chin which can be adjusted to engage a patient's chin accurately and snugly. In other words, it is an object of the invention to provide a cervical brace in which the chin support member is adjustable forwardly and backwardly relative to the wearer. It is also an object of the invention to provide a cervical brace which, as well as supporting the chin, also supports the head. A further object of the invention is to provide a cervical brace which can be relatively easily fitted and removed. Another object of the invention is to provide a cervical brace in which the chin support member is removable.

SUMMARY OF THE INVENTION

According to the invention there is provided a cervical brace comprising a torso engaging member having a back portion and a front portion, the front portion in use being adjacent to the front of the torso and the rear portion, in use, being adjacent to the back of the torso, a chin support member for engaging and supporting the chin of the wearer, mounting means for mounting the chin support member to the torso engaging member so that the chin support member is movable backwardly and forwardly relative to the torso engaging member for accommodating, in use, different positions of a wearer's chin.

In one embodiment of the invention the mounting means releasably mounts the chin support member to the torso engaging member.

Preferably, the mounting means comprises a strut extending at one end from the chin support member, and being pivotly connected at the other end to the front portion of the torso engaging member.

Advantageously, a brace member extends from the strut, and engages the front portion of the torso engaging member at a position spaced apart from the pivotal mounting of the strut, adjusting means being provided on the brace member for adjusting the length thereof.

In one embodiment of the invention the brace member engages the front portion of the torso engaging member rearwardly of the strut.

In another embodiment of the invention an adjusting means is provided in the strut to adjust the length of the strut.

Preferably, the torso engaging member comprises a harness having a framework which comprises a front member, a rear member, and a pair of side members extending between the front and rear members, the strut being pivotly mounted on the front member.

Advantageously, four head supporting uprights extend upwardly from the framework to, in use, extend adjacent the front sides and rear sides of wearer's head, and the head supporting uprights are releasably engagable with the framework.

ADVANTAGES OF THE INVENTION

The advantages of the invention are many. In particular, one important advantage of the invention is that it provides a cervical brace which comprises a torso engaging member and a chin support member whereby the chin support member can be adjusted both upwardly and downwardly, and, inwardly and outwardly relative to the wearer, so that the chin support member can be adjusted to correctly and snugly engage the wearer's chin. Another advantage of the invention is that by virtue of the fact that the chin support member and strut are releasable from the torso engaging member, the chin support member and strut can be removed entirely from the torso engaging member should this be desired. In this case a wearer could continue to wear the torso engaging member which is relatively comfortable, and in due course re-fit the chin support member. This is a particular advantage, if one wished to remove the chin support member for a short period of time. This could be done without the need to remove the harness entirely. This is a particular advantage where one wishes to merely remove the chin support member for a short period of time. Indeed, it is generally believed that one may be able to avoid whiplash injury should they have their head supported relative to the torso of the body. Accordingly, it is envisaged in certain cases that drivers may continuously wear the harness, and when actually driving a vehicle could mount the chin support member on the harness, and accordingly support their chin, and in turn, their head while driving. This, it is envisaged would considerably reduce the number of whiplash injuries in accidents. It is also felt that if the head could be restricted from rotating about the neck, less damage would be done in the event of a road accident. Thus, the continuous wearing of the head supporting upright while driving it is also believed would considerably reduce injuries in the event of a road accident.

Another advantage of the invention is achieved when the head supporting uprights are provided. In this case, the individual's head is adequately supported, and should the individual be subjected to a shock when wearing the head supporting uprights, the head will be sufficiently supported to avoid any dislocation of vertebrae or any other injury to the wearer. A typical example of where this advantage will be achieved is where the wearer is wearing the device with the head supporting uprights while in a car accident. In fact, it is envisaged that the head supporting uprights will have particular advantage to a wearer who has previously suffered a whiplash injury, in that if they are subjected to further shock, it is envisaged that no further damage or injury will be received.

A further advantage of the invention is that by virtue of the fact that the cervical brace comprises a chin support member mounted on a single strut extending upwards from the harness the cervical brace according to the invention, can be worn quite unobtrusively. Indeed, in general, it is virtually unnoticeable when being worn. This is a considerable advantage in that people who may be self-conscious of wearing conventional cervical collars do not suffer from the same difficulties when wearing the cervical brace according to the present invention.

These, and other objects and advantages of the invention will be readily apparent from the following description of a preferred embodiment thereof given by way of example only with reference to the accompanying drawings.

BRIEF DESCRIPTION OF THE DRAWINGS

FIG. 2 is a perspective view of portion of the cervical brace of FIG. 1 in use, FIG. 4 is a perspective view of a further portion of the cervical brace of FIG. 1, FIG. 6 is a perspective view of the cervical brace of FIG. 1 with a further additional attachment mounted thereto, FIG. 7 is a perspective view of the attachment illustrated in FIG. 6, and FIG. 8 is a side view of a detail of the cervical brace of FIG. 1.

DETAILED DESCRIPTION OF THE INVENTION

Figures 1, 3:
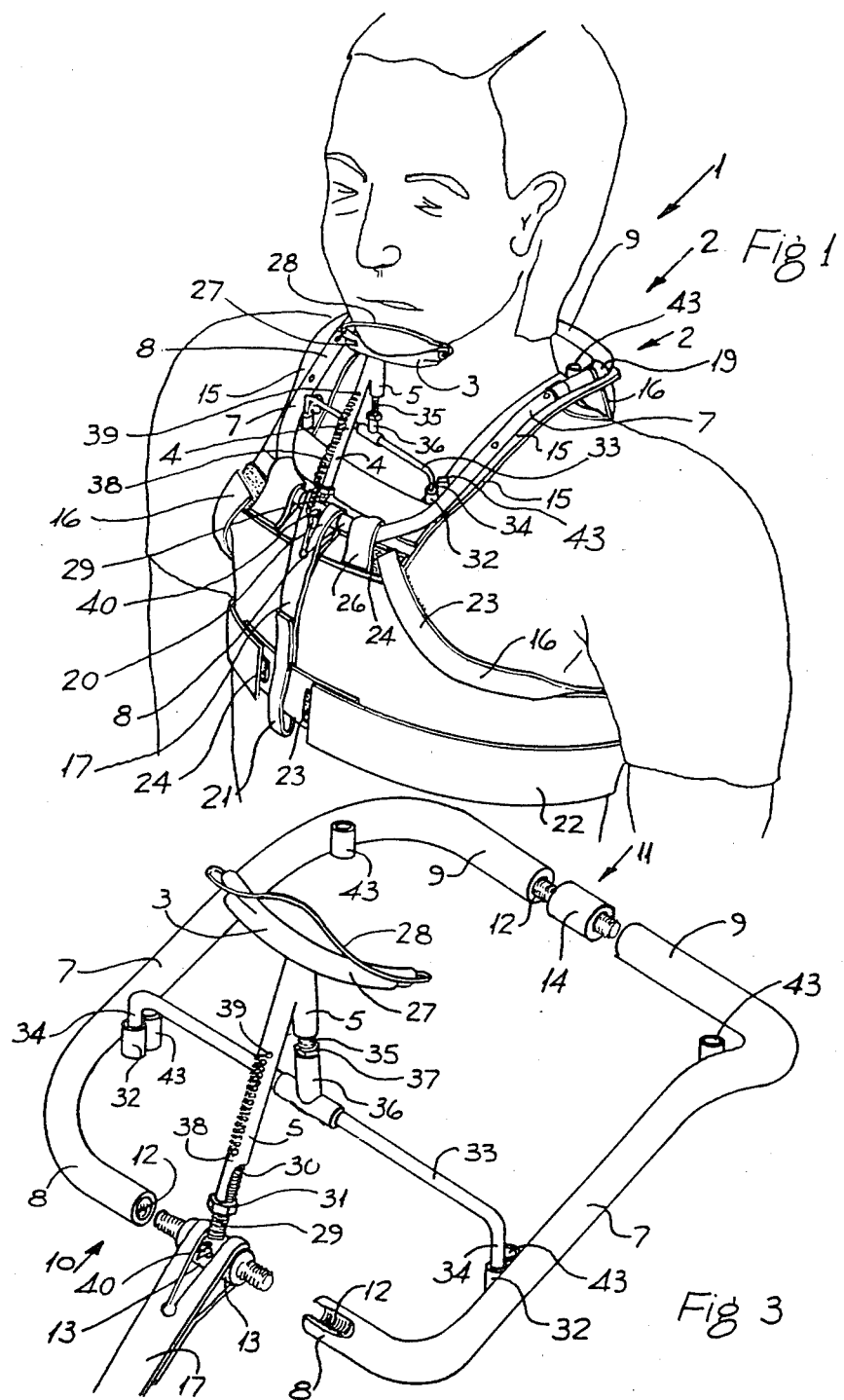
FIG. 1 is a perspective view of a cervical brace according to the invention in use.
FIG. 3 is a perspective view of another portion of the cervical brace of FIG. 1.

Referring to the drawings, there is provided a cervical brace according to the invention, indicated generally by the reference numeral 1. The cervical brace comprises a torso engaging member, which, in this case, is provided by a harness 2, which supports a chin support member 3 on mounting means.

The mounting means comprises a strut 4, of tubular steel, which extends from the chin support member 3, and releasably engages the harness 2. A brace member 5 of tubular steel extends from the strut 4 and permits adjustment of the chin support member 3 inwardly and outwardly relative to the wearer. The strut 4 and brace member 5 are described in more detail below.

The harness 2 comprises a framework having a pair of side members 7 joined by front and rear members 8 and 9 respectively. In this particular case, the side members 7 and the front and rear members 8 and 9 are of tubular plastics material and are formed in two pieces joined at 10 and 11 at the front and rear members 8 and 9 respectively. Turn buckle screws 13 and 14 engage left and right hand threaded bores 12 in the front and rear members 8 and 9 to permit the side members 7 to be adjusted towards and away from each other. Furthermore, the use of the turn buckle screws 13 and 14 facilitates fitting the harness 2, for example, to an accident victim where it is desired not to disturb the victim. The two halves of the framework formed by the side member 7 and portions of the front and rear members 8 and 9 may be offered on each side of the neck of the victim, and secured by tightening the turn buckle screws 13 and 14.

A padded member 15 of leather material is secured to the framework 5. Straps 16 and 17 extending from the front and rear members 8 and 9 and the member 15 secure the harness 2 around the upper torso of the wearer, as illustrated in FIGS. 1 and 2. Loops 19 on the straps 16 engage the rear of the side members 7, and the straps 16 extend under the armpits of a wearer to releasably engage the front portion of the padded member 15. Loops 20 on the straps 17 engage the front and rear members 8 and 9, and releasable loops 21 on the other end of the strap 17 releasably engage a belt 22 which is worn around the upper torso of the body. Strips 23 and 24 of hooks and eyes fasteners of the type sold under the trade name VELCRO form releasable and adjustable securing means for releasably and adjustably securing the straps. Strips 23 of the VELCRO are provided on the free ends of the straps 16 to engage corresponding strips 24 of the VELCRO on the padded member 15 at the front portion thereof. The free ends of the straps 17 which form the loops 21 are also provided with strips 23 and 24 of VELCRO to accommodate releasable securing of the loops 21, and also to provide for adjustment of the length of the straps 17. Strips of VELCRO 23 and 24 are provided on the free ends of the belt 22 for securing the belt around the torso of the wearer. Straps 26 extending from the member 15 secure the framework of the harness 2. The straps 26 are releasably secured to the member 15 by strips 23 and 24 of VELCRO.

The chin support member 3 comprises an arcuate member 27 of plastic coated metal which engages the wearer beneath the chin, as illustrated in FIG. 1. A front member, in this case provided by a plastic coated wire 28 of arcuate shape extends from the ends of the arcuate member 27 to engage the front portion of the wearers chin. This prevents the chin from extending out over the arcuate member 27. The strut 4 extending from the arcuate member 27 releasably engages the harness 2 by means of an adjusting means, namely, an adjusting screw 29 extending from the front turn buckle screw 13. Accordingly, the strut 3 is pivotal on the front member 8 by rotating the turn buckle screw 13. The screw 29 slidably and releasably engages a bore 30 in the strut 4. A nut 31 on the screw 29 permits adjustment of the effective length of the strut 3, thus providing height adjustment of the chin support member 3. The brace member 5 extending from the strut 4 engages a cross member 33 extending between the side members 7 of the harness 2. Sockets 32 on the side members 7 releasably engage ends 34 of the cross members 33. Adjustment means provided by a threaded portion 35 extending from the brace member 5 slidably and releasably engages a socket 36 on the cross member 33. A nut 37 on the threaded portion 35 permit adjustment of the relative length of the brace member 5 extending from the socket 36. By adjusting the effective length of the brace member 5, the strut 4 is pivoted, thereby allowing angular adjustment of the strut and chin support member 3 towards and away from the wearers chin. A spring 38 extending from an anchor point 39 on the strut 4 releasably engages a hook 40 on the turn buckle 13, and secures the strut 4 in engagement with the adjusting screw 29, while downward pressure of the chin of the wearer retains the brace member 5 in engagement with the socket 36.

Figure 5:
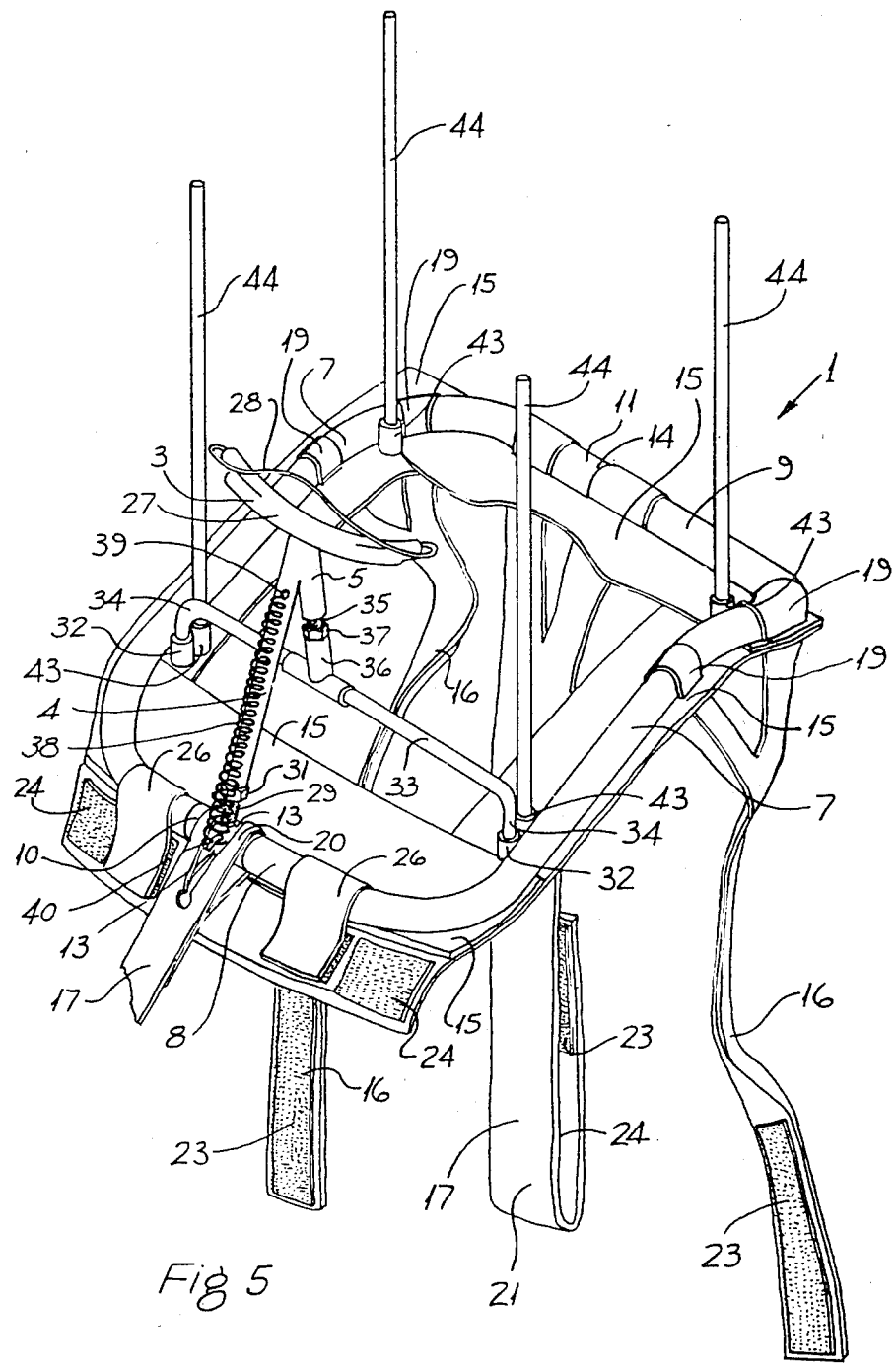
FIG. 5 is a perspective view of the cervical brace of FIG. 1 with additional attachments mounted thereto.

Four sockets 43 on the side members 7 releasably engage four head supporting uprights 44 as illustrated in FIG. 5, to restrict the rotational movement of the head about the neck, and also to restrict front and back and sideward movement of the head. Referring now to FIGS. 6 and 7 there is illustrated a head support member 50 for supporting the back of the head. The head support member is releasably engagable with the framework, and engages the sockets 43 at the rear of the side members 7. The head support member 50 comprises a pair of upstanding members 51 which are cranked at 52. A cross bar 53 extends between the upstanding members 51. An arcuate cross member 54 which is provided with a padded surface 55 is mounted on the cross bar 53 by adjusting means, in this case provided by adjusting screws 56. The screws 56 engage threaded holes 57 in the cross bar 53 for adjusting the position of the cross member 54 towards and away from the back of the head. The upstanding members 51 releasably engage the sockets 43 when it is desired to use the head support member 50.

In use, the harness 2 is first fitted to the upper torso of the body of the wearer and strapped in position with the straps 16 and 17 and the belt 22 which are secured with the desired adjustment by the VELCRO strips 23 and 24, see FIGS. 1 and 2. The chin support member 3, the strut 4 and the brace member 5 are then assembled to the harness 2 by engaging the strut 4 on the screw 29 and the threaded portion 35 in the socket 36. The spring 38 is secured on the hook 40. The nuts 31 and 37 are adjusted so that the chin support member 3 engages the chin of the wearer in the desired position, and at the desired height. Should it be desired, the head support uprights 44 may be used by engaging them in the sockets 43.

After the harness 2 has been secured to the wearer, a shirt, blouse, jumper or the like may be worn over it, thus totally concealing the harness. The harness may worn directly over the wearer's skin. If desired, the chin support member 3, the strut 4, and the brace member 5 may be removed by releasing the spring 38 from the hook 40. Thus, where one desires not to wear the chin support member 3 for a short period of time, this may be removed without the need for removing the entire harness 2.

Should it be desired to use the head support member 50, the upstanding members 51 are engaged in the sockets 43. The arcuate cross member 54 is then adjusted by the adjusting screws 56 so that the cross member 54 comfortably abuts the back of the wearers head.

It will be appreciated that while a particular construction of framework and strap arrangement has been described for the harness, any other suitable framework or strap arrangement could be used. Indeed, in certain cases it is envisaged that the framework may be dispensed with altogether and the harness might merely comprise a strap arrangement. In another case, it is envisaged that the strap arrangement may be dispensed with, and the framework could provide the harness. Needless to say, it will be appreciated that any suitable torso engaging member besides a harness could be used. Where a framework is used, it will be appreciated that any construction of framework could be used without departing from the scope of the invention, for example, instead of the framework being provided in two parts it could be provided in a single part, or in many more than two parts. Needless to say, where it is provided in two parts, it is not necessary that two parts should be adjustable inwardly and outwardly by means of a turn buckle screw. It will also, of course, be appreciated that other suitable construction chin support members could be provided without departing from the scope of the invention. Needless to say, a mounting means other than a strut and brace could be provided for mounting the chin support member. Where a strut is provided, other suitable shapes and constructions of strut could be used without departing from the scope of the invention. Needless to say, while it is advantageous, it is not necessary for the strut to be releasably mounted to the harness. Similarly, it will be appreciated that in certain cases, the harness, the strut and chin support member need not be releasably connected together.

It will also of course, be appreciated, that it is not necessary for the strut to be adjustable in length, and where an adjustable strut is provided, any other adjusting means and indeed mounting means could be used besides that described. Indeed, in certain cases, it is envisaged that the spring may be dispensed with altogether, and a turn buckle may be provided in the strut, or at one or other end of the strut, to accommodate length adjustment of the strut. Furthermore, other adjustment means for adjusting the length of the brace member may be provided.

It is also envisaged that instead of pivotally mounting the strut for in and out movement of the chin support member, the chin support member could be mounted on the strut to be slidable inwardly and outwardly relative to the strut. Indeed, any other mounting means for mounting the chin support to the torso engaging member so that the chin support member is movable inwardly and outwardly relative to the wearer, could be provided without departing from the scope of the invention.

While the cervical brace has been described with head supporting uprights which are releasably mounted in sockets to the harness, the uprights could be dispensed with altogether, and where they are required in certain cases, they could be permanently mounted to the harness if desired. Additionally, it will be appreciated that while a front member has been provided on the chin support member, this is not necessary. Indeed, in certain cases, it is envisaged that other suitable support members for supporting other parts of the head, face, neck or the like could be provided, for example, in certain cases, support members to support the head adjacent the back of the neck, or at the back of the head could be provided.

It is also envisaged that other suitable means for securing the straps besides VELCO could be used. In certain cases, it is envisaged that buckles may be used.

While in the embodiment of the invention described, the harness has been worn relatively high up on the torso, in other words, the belt 22 extends more or less around the chest of the wearer, it is envisaged that the belt 22 could be worn around the waist of the wearer, indeed, in certain cases envisaged that two belts, one at the chest, and one at the waist could be provided.

Further, it will be appreciated that the cervical brace may be provided without the head supporting uprights and/or the head support member without departing from the scope of the invention. Furthermore, it will be appreciated that other suitable mounting arrangements for the head support member could be used. For example, in certain cases, it is envisaged that the head support member may be fixedly engaged to the framework rather than releasably engaged. It will also, of course, be appreciated that the arcuate cross member could be rigidly mounted to the upstanding members without any adjustment, if desired.

We claim:

1. A cervical brace comprising:
   a torso engaging member having a back portion and a front portion, the front protion, in use, being adjacent to the front of the torso and the rear portion, in use, being adjacent to the back of the torso;
   a chin support member for engaging and supporting the chin of the wearer; and
   mounting means for mounting the chin cupport member to the torso engaging member, the mounting means comprising a strut and a brace member each supporting the chin support member, said strut having one end operatively coupled with the chin supporting member, and being pivotally connected at the other end to the front portion of the torso engaging member so that the chin support member is movable backwardly and forwardly relative to the torso engaging member for accomodating, in use, different positions of a wearer's chin, said brace member operatively coupled at one end to the chin support member, and engaging at the other end a front portion of the torso engaging member at a position spaced rearwardly from the pivotal mounting of the strut, adjusting means being provided on the brace member for adjusting the length thereof.

2. A cervical brace as claimed in claim 1 in which the mounting means releasably mounts the chin support member to the torso engaging member.

3. A cervical brace as claimed in claim 1 in which the brace member engages the front portion of the torso engaging member rearwardly of the strut.

4. A cervical brace as claimed in claim 1 in which the adjusting means is provided by an adjusting screw and nut mounted in the brace member.

5. A cervical brace as claimed in claim 1 in which dusting means is provided in the strut to adjust the length of the strut.

6. A cervical brace as claimed in claim 5 in which the adjusting means for adjusting the strut length comprises a screw and nut mounted in the strut.

7. A cervical brace as claimed in claim 1 in which the chin support member comprises a transverse member of arcuate shape for engaging beneath the chin, and a front member for arcuate shape extending from the ends of the transverse member to engage the front of the chin.

8. A cervical brace as claimed in claim 1 in which the torso engaging member comprises a harness having a framework which comprises a front member, a rear member, and a pair of side members extending between the front and reaar members, the strut being pivotally mounted on the front member.

9. A cervical brace as claimed in claim 8 in which four head supporting uprights extend upwardly from the framework to, in use, extend adjacent the front sides and rear sides of wearers head.

10. A cervical brace as claimed in claim 9 in which the head supporting uprights are releasably engagable with the framework.

11. A cervical brace as claimed in claim 10 in which four mounting sockets are provided in the framework, two on each side member to releasably engage the head supporting uprights.

12. A cervical brace as claimed in claim 8 in which a cross member extends between the side members intermediately front and rear members to engage the brace member.

13. A cervical brace as claimed in claim 8 in which the front and rear members are joined intermediate their ends each by a turn buckle, the turn buckle of the front member forming the pivot mounting of the strut.

14. A cervical brace as claimed in claim 8 in which the harness comprises a strap extending from the rear of each side member to each end of the front portion of the harness, to, in use, extend under the armpits of the wearer, the straps being releasably engagable with the front portion or side members.

15. A cervical brace as claimed in claim 14 in which the harness comprises a torso engaging belt which, in use, extends around the torso, the ends of the belt being releasably engagable, and a front strap extending from the front member engagable with the torso engaging belt, and a rear strap extending from the rear member to engage the torso engaging belt.

16. A cervical brace as claimed in claim 8 in which a head support member for supporting the back of the head is provided, the head suppor member comprising a cross member for engaging the back of the head, and a pair of upstanding members extending from the framework to support the cross member.

17. A cervical brace as claimed in claim 16 in which the upstanding members are releasably engagable with the framework.

18. A cervical brace as claimed in claim 16 in which adjustment means are provided to mount the cross member to the upstanding members for adjustment of the cross member relative to the upstanding members.

* * * * *